(12) United States Patent
Zibert et al.

(10) Patent No.: US 9,402,823 B2
(45) Date of Patent: Aug. 2, 2016

(54) INGENOLS FOR TREATING SEBORRHEIC KERATOSIS

(75) Inventors: John Zibert, Ballerup (DK); Kresten Skak, Ballerup (DK); Inge Boe, Ballerup (DK)

(73) Assignee: LEO Laboratories Limited, Dublin (IE)

( * ) Notice: Subject to any disclaimer, the term of this patent is extended or adjusted under 35 U.S.C. 154(b) by 0 days.

(21) Appl. No.: 13/995,177

(22) PCT Filed: Dec. 16, 2011

(86) PCT No.: PCT/EP2011/073046
§ 371 (c)(1),
(2), (4) Date: Sep. 9, 2013

(87) PCT Pub. No.: WO2012/080466
PCT Pub. Date: Jun. 21, 2012

(65) Prior Publication Data
US 2013/0338226 A1    Dec. 19, 2013

Related U.S. Application Data

(60) Provisional application No. 61/424,409, filed on Dec. 17, 2010.

(51) Int. Cl.
*A61K 31/21* (2006.01)
*A61K 31/215* (2006.01)
*A61K 8/37* (2006.01)
*A61K 9/00* (2006.01)
*A61K 31/335* (2006.01)
*A61Q 19/00* (2006.01)
*A61K 31/55* (2006.01)
*A61K 47/10* (2006.01)
*A61K 47/38* (2006.01)

(52) U.S. Cl.
CPC ............... *A61K 31/215* (2013.01); *A61K 8/375* (2013.01); *A61K 9/0014* (2013.01); *A61K 31/335* (2013.01); *A61Q 19/00* (2013.01); *A61K 31/55* (2013.01); *A61K 47/10* (2013.01); *A61K 47/38* (2013.01)

(58) Field of Classification Search
CPC ......................................................... A61K 31/55
USPC ........................................................ 514/511
See application file for complete search history.

(56) References Cited

FOREIGN PATENT DOCUMENTS

| WO | WO-99/08994 | 2/1999 |
|---|---|---|
| WO | WO-01/93884 | 12/2001 |
| WO | WO-02/11743 | 2/2002 |
| WO | WO-2006/063382 | 6/2006 |
| WO | WO-2007/059584 | 5/2007 |
| WO | WO-2008/131491 | 11/2008 |
| WO | WO-2010/091472 | 8/2010 |
| WO | WO-2011/128780 | 10/2011 |

OTHER PUBLICATIONS

Ersvaer et al., "The Protein Kinase C Agonist PEP006 (Ingenol 3-Angelate) in the Treatment of Human Cancer: A Balance between Efficacy and Toxicity", Toxins, vol. 2, pp. 174-194 (Jan. 2010).*
"Seborrheic Keratoses", the Merck Manual of Diagnosis and Therapy, 1987, Merck Sharp & Dohme Research Laboratories, pp. 2305 (1987).
Anderson et al., "Randomized double-blind, double-dummy, vehicle-controlled study of ingenol mebutate gel 0.025% and 0.05% for actinic keratosis", Journal of the American Academy of Dermatology, vol. 60, No. 6, pp. 934-943 (2009).
International Search Report and Written Opinion dated Jun. 19, 2012, in corresponding PCT Application No. PCT/EP2011/073046.

* cited by examiner

*Primary Examiner* — Kevin E Weddington
(74) *Attorney, Agent, or Firm* — Fish & Richardson P.C.

(57) ABSTRACT

The invention provides ingenol compounds for treating seborrheic keratosis.

50 Claims, 3 Drawing Sheets

FIG. 1

Clearence

|  | Cleared Lesions | Percent Cleared | Affected Patients |
|---|---|---|---|
| Occluded | 8 / 40 | 20% | 8 patients |
| Alcohol Prepared | 6 / 40 | 15% | 5 patients |
| Total | 14 / 80 | 17.5% | 10 patients |

INGENOLS FOR TREATING SEBORRHEIC KERATOSIS

CROSS-REFERENCE TO RELATED APPLICATIONS

This application is the U.S. national phase application pursuant to 35 U.S.C. §371 of PCT International Patent Application No. PCT/EP2011/073046, filed Dec. 16, 2011, which claims the benefit of U.S. Provisional Patent Application No. 61/424,409, filed Dec. 17, 2010. The entire contents of the aforementioned patent applications are incorporated herein by this reference.

BACKGROUND OF THE INVENTION

Ingenol compounds are previously described for treatment of cancer and actinic keratosis in WO99/08994, WO01/93884, WO06/063382 and WO02/11743. Treatment of other lesions of the skin are described in WO2007/059584, WO2008/131491 and WO2010/091472.

seborrheic keratosis is as such a benign skin condition. However, treatment of the condition is often pursued for cosmetic purposes. Treatment of the condition by removing the growth is typically by cryosurgery. Small lesions can be treated with light electrocautery. Larger lesions can be treated with electrodessication and curettage, shave excision, or cryotherapy. Removal of seborrheic keratoses will cause some visible scarring especially in persons with dark skin tones. Also the removal of the growths are performed at specialised clinics.

The present invention provides a treatment of seborrheic keratosis, which is very easy to perform at home. The patient is typically treated only a few days, and the treatment leaves the skin with little or no scarring.

DESCRIPTION OF THE DRAWINGS

FIG. 1: clearance

SUMMARY OF THE INVENTION

Figure 2:
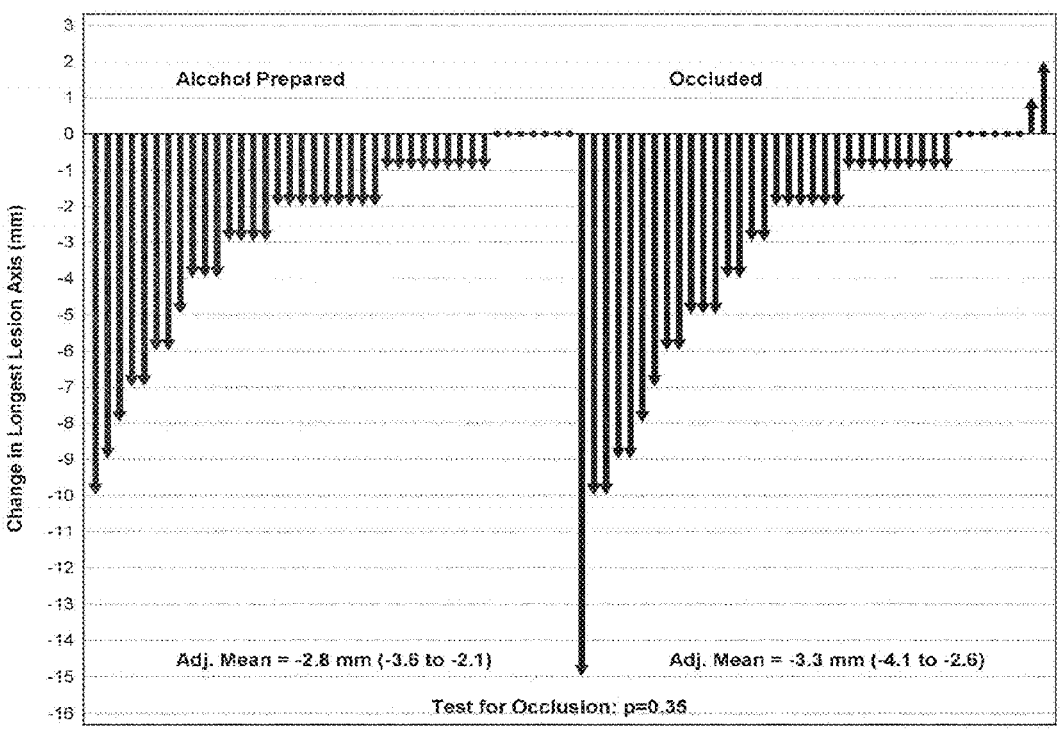
FIG. 2: change in the longest axis of lesions
Figure 3:
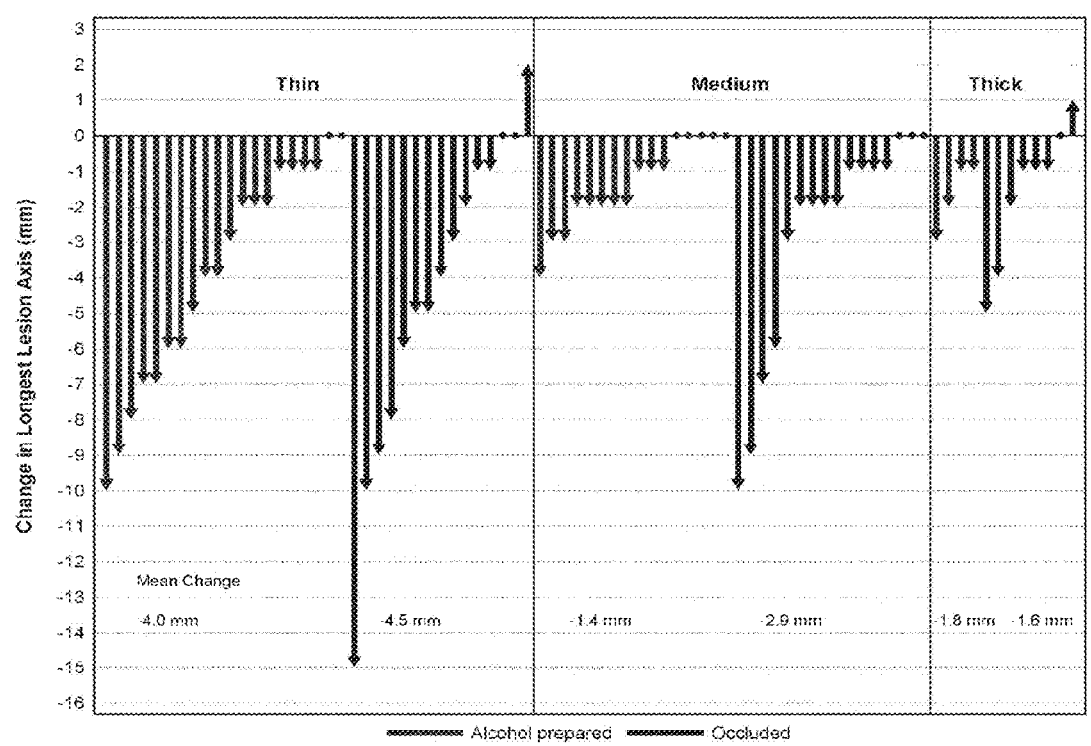
FIG. 3: Change in the longest axis—thickness.

In an embodiment the invention comprises an ingenol compound for use in treating seborrheic keratosis in a subject.

In an embodiment the invention comprises an ingenol compound for use in treating benign skin growth or benign tumor.

In an embodiment the invention embraces the use of an ingenol compound for the manufacture of a medicament for treatment of seborrheic keratosis in a subject.

In an embodiment the invention embraces the use of an ingenol compound for the manufacture of a medicament for treatment of benign skin growth or benign tumors.

An embodiment the invention embraces a method for the treatment of seborrheic keratosis in a subject comprising administration of an ingenol compound.

An embodiment the invention embraces a method for the treatment of benign skin growth or benign tumors in a subject comprising administration of an ingenol compound.

In an embodiment the invention embraces a topical composition for use in treating seborrheic keratosis in a subject comprising an ingenol compound.

In an embodiment of any of the embodiments above, the ingenol compound is ingenol-3-angelate.

In an embodiment of any of the embodiments above, the invention embraces an ingenol compound together with a pharmaceutically acceptable carrier.

In an embodiment of any of the embodiments above, the ingenol compound is used in topical application.

In an embodiment of any of the embodiments above, the ingenol compound is administered in the form of an isopropyl based gel or a macrocetyl ether cream.

In an embodiment of any of the embodiments above the ingenol compound is administered in an isopropyl based gel. In an embodiment the isopropyl based gel contains ingenol compound in a concentration of from 0.01%-0.1%. In an embodiment the concentration is from 0.01%-0.05%. In an embodiment the concentration is 0.05%.

In an embodiment of any of the above embodiments, the ingenol compound is administered to the subject as one, two or three applications on 1, 2 or 3 consecutive days. In an embodiment the ingenol compound is administered to the subject as three applications on 3 consecutive days.

In an embodiment of any of the above embodiments, the ingenol compound is applied to the lesion. In embodiments of the invention the lesion is pre-treated with an alcohol swab before application. In another embodiment of the invention the lesion is occluded after application of the ingenol compound.

In an embodiment according to any of the above embodiments, the lesion is diminished on the length of the longest axis.

DETAILED DESCRIPTION OF THE INVENTION

As used herein the singular form "a", "an", and "the" include plural aspects unless the context clearly dictates otherwise. Thus, for example, reference to "an ingenol compound" or includes a single compound, as well as two or more compounds as appropriate.

As used herein, the term "treatment" is intended to refer to regression, elimination, partial or full removal or detachment, clearance, reduction in size (e.g. surface area or volume), or otherwise desired decrease in size number or growth rate. Also treatment in the context of the present invention could refer to an improvement in the appearance of seborrheic keratosis or the improvement in the appearance of the treated skin area such as lack of scarring of the tissue.

Seborrheic keratoses may be divided into the following types:

Common seborrheic keratosis (Basal cell papilloma, Solid seborrheic keratosis)
Reticulated seborrheic keratosis (Adenoid seborrheic keratosis)
Stucco keratosis (Digitate seborrheic keratosis, Hyperkeratotic seborrheic keratosis, Serrated seborrheic keratosis, Verrucous seborrheic keratosis)
Clonal seborrheic keratosis
Irritated seborrheic keratosis (Basosquamous cell acanthoma, Inflamed seborrheic keratosis)
Seborrheic keratosis with squamous atypia
Melanoacanthoma (Pigmented seborrheic keratosis)
Dermatosis papulosa nigra And it is intended that the present invention "seborrheic keratosis" includes all subtypes and subdivisions. Some dermatologists refer to seborrheic keratoses as "seborrheic warts", however these lesions are usually not associated with HPV.

The invention also provides a method for treating benign skin growth or benign tumors. In embodiments of the invention this includes improvement of scars and pigmentet as well as unpigmented lesions. In an embodiment this includes skin tags, lentigo and melasma.

Ingenol compound refers to compounds having C3, C4, C5-trioxy trans bicycle[4.4.1]-undecane ingenane skeleton. Such compounds are extensively reported and known in the literature and can be isolated from plants including but not limited to as from a species of the family Euphorbiaceae. All racemates and isomers are contemplated herein. Derivatives of this ingenane skeleton has been described for example in WO02/11743, WO01/93884, WO2008/131491, and WO2010/091472. In an embodiment of the invention the ingenol compound is ingenol-3-angelate (PEP005).

Ingenol compounds includes for example pharmaceutically acceptable salts of the above mentioned compounds. Such salts include, but are not limited to, salts of pharmaceutically acceptable inorganic acids such as hydrochloric, sulphuric, phosphoric, nitric, carbonic, boric, sulfamic and hydrobromic acids or salts of pharmaceuticaly acceptable organic acids such as acetic, propionic, butyric, tartaric, maleic, hydromaleic, fumaric, maleic, citric, lactic, mucic, gluconic, benzoic, succinic, oxalic, phenylacetic, methanesulphonic, toluenesulphonic, benzenesulphinic, salicyclic, sulphanilic, aspartic, glutamic, edetic, stearic, palmitic, oleic, lauric, pantothenic, tannic, ascorbic and valric acids.

Ingenol compounds of the invention may by in crystalline form either as the free compounds or as solvates as described in WO2011/128780 and it is intended that all forms are within the scope of the present invention.

The ingenol compounds are administered to the subject in treatment effective amounts. Suitable effective amounts for administration and dosing regiments can be determined by the attending physician and may depend on the appearance of the severity of the condition, the location, the area to the treated and the general health of the subject.

Lesions on non-head locations have been treated with 0.05% by weight of ingenol-3-angelate in an isopropyl alcohol based gel. Patients were treated for 3 consecutive days and the lesions were sweeped with an alcohol swab before application of the gel.

Medicament of compositions suitable for use in the invention may contain the ingenol compound in an amount of from about 0.0001% to 100% by weight. In embodiments of the invention the compositions contain the ingenol compound in an amount of from about 0.0001% to about 10% by weight, for example about 0.0005, 0.001, 0.0025, 0.005, 0.0075, 0.01, 0.0125, 0.015, 0.02, 0.025, 0.05, 0.075, 0.1, 0.125, 0.15, 0.2 or 0.25% to about 0.5, 1.0, 2.5 or 5.0%. In an embodiment of the invention the ingenol compound is ingenol-3-angelate present in an amount of about 0.001 to about 1%. In an embodiment of the invention the ingenol compound is ingenol-3-angelate present in an amount of about 0.005 to about 0.2%. In an embodiment of the invention the ingenol compound is ingenol-3-angelate present in an amount of about 0.005 to about 0.1%. In an embodiment of the invention the ingenol compound is ingenol-3-angelate present in an amount of about 0.015% or 0.05%. In an embodiment the amount present is 0.05%.

The dosage on application will depend on a number of factors that may readily be determined by the skilled person, but may be one or more doses per day, with a course of treatment lasting from one day to several months, or until the desired effect is achieved. In an embodiment the ingenol compound is administered topically once a day for 3 consecutive days.

Whilst the lesions to be treated may be of any size and covering in principle an unlimited area, in an embodiment of the invention the skin surface area to be treated is 500 $mm^2$ or less. In an embodiment the skin surface area to be treated is 250 $mm^2$ or less. In an embodiment the skin surface area to be treated is 150 $mm^2$ or less. In an embodiment the skin surface area to be treated is 100 $mm^2$ or less. In an embodiment the skin surface area to be treated is 75 $mm^2$ or less, or 50, 25 or 10 $mm^2$ or less.

The present invention is contemplated to be applied to the area of the affected skin. However, the invention is not limited as to application to the surrounding skin.

In an embodiment the ingenol compound is administered topically to the area requiring treatment. Any area of the skin requiring treatment may be treated according to the invention.

The ingenol compounds may be applied topically in any suitable form including solutions, emulsions (oil-in-water, water-in-oil, aerosols or foams), ointments, pastes, lotions, powders, paints, gels, hydrogels, hydrocolloids and creams may be prepared to as to contain liposomes, micelles, and/or microspheres. In an embodiment the ingenol compound is applied in a gel as described in WO2007/068963. Alternatively, the ingenol compounds may be presented in the form of an active occlusive dressing, e.g., where the ingenol compound is impregnated or coated on a dressing such as bandages, gauzes, tapes, nets, face masks, adhesive plaster, films, membranes or patches.

The formulation of compositions and dressings contemplated herein is well known to those skilled in the art, see for example Remington's Pharmaceutical Sciences, $18^{th}$ addition, Mack Publishing, 1990.

In an embodiment of the invention, the ingenol compound may be topically applied in the form of an isopropyl alcohol-based gel having 0.05% by weight of ingenol compound. One suitable formulation includes isopropyl alcohol, benzyl alcohol, a cellulose polymer, such as hydroxyethyl cellulose and buffer (e.g. citrate) at a pH<3. In another embodiment of the invention, the ingenol compound can be formulated for topical application in the form of a macrocetyl ether cream for example containing cetomacrogel emulsifying wax, white soft paraffin and liquid paraffin. Embodiments of the invention are disclosed and described in WO 2007/068963. For example, the formulations disclosed contain benzyl alcohol 0.9%, isopropyl alcohol 30%, citrate buffer 67%, HEC HHX 1.5% at pH of 2.5-4.0.

It is to be understood that the present invention can be applied alone or in combination with other known treatments for seborrheic keratosis. The administration can either be as subsequent treatment steps or simultaneously applied. The different treatments can, wherein appropriate be formulated together in one composition or they can be applied separately, either sequentially or together.

Examples

Treatment of Patients with Seborrheic Keratosis on Non-Head Locations

Inclusion criteria for the clinical trial was two or four seborrheic keratosis lesions suitable for treatment (half the lesions are occluded and the remainder non-occluded) on non-head locations (trunk and extremities).

All eligible patients were to receive PEP005 Gel, 0.05%, on Days 1, 2 and 3. Each patient were to be assessed prior to each treatment on Day 2 and 3 as to whether they are tolerating the study medication (e.g., do not have LSRs or AEs that would preclude treatment). If tolerability to study medication was maintained, the patients were to receive all three doses of PEP005 Gel, 0.05%, regardless of whether the seborrheic keratosis being treated has resolved or not.

Subsequent follow-up visits for safety assessments were made on Days 4 (as applicable), 8, 15, 29 and 43. Efficacy assessments were conducted at Baseline and Day 43.

Of the seborrheic keratosis lesions suitable for treatment:

Half of the selected lesions were cleaned by use of an alcohol swab and allowed to air dry prior to application of the Day 1 dose only. These lesions were then to have sufficient study medication applied directly to the seborrheic keratosis lesions with no margin added.

The other half of the selected lesions were to have sufficient study medication applied directly to the seborrheic keratosis lesions with no margin added. The treated lesions must be then allowed to dry for 15 minutes following application of PEP005 Gel before covering the treated lesion(s) with a dressing provided with the study medication.

Results

Primary outcome measures are determined as treatment related Adverse Events (AEs), local skin responses (LSR); and scarring. As secondary outcome measure are determined length of longest lesion axis.

The majority of patients received all three applications of the compound. Local skin responses peaks within the first week. There is no scarring of the affected skin. A few, mild adverse events were observed.

Of the treated lesions 80% were reduced in size and 18% of the lesion were completely cleared.

The invention as demonstrated by the administration regimens as described shows a reduction in the lesions length as measured on the longest axis of the lesions by 2.8 and 3.3 mm. (alcohol prepared/occluded)

The invention as demonstrated by the administration regimens described below shows an efficacy of the present administration that has shown greatest effect on thin lesions as measured as reduction in length of the longest axis. The change was 4.0 mm and 4.5 mm (alcohol prepared/occluded).

The present administration regimen showed less reductions in lesions as measured by reduction in length of the longest axis on medium thick lesions of 1.4 mm and 2.9 mm (alcohol prepared/occluded), and even less effect on thick lesions which was 1.8 mm and 1.6 mm (alcohol prepared/occluded).

The invention claimed is:

1. A method for the treatment of seborrheic keratosis lesions in a subject,
the method comprising topically administering an ingenol compound to the seborrheic keratosis lesions to treat the seborrheic keratosis lesions, wherein the seborrheic keratosis lesions are not associated with HPV.

2. The method of claim 1, wherein said ingenol compound is ingenol-3-angelate.

3. The method according to claim 1, wherein the ingenol compound is administered in the form of an isopropyl alcohol based gel.

4. The method according to claim 1, wherein the ingenol compound is present in a concentration of about 0.05%.

5. The method according to claim 3, wherein the isopropyl based gel further includes benzyl alcohol, a cellulose polymer and a buffer.

6. The method according to claim 5, wherein the cellulose polymer is hydroxyethyl cellulose.

7. The method according to claim 5, wherein the buffer is citrate.

8. The method according to claim 5, wherein the isopropyl based gel has a pH<3.

9. The method according to claim 5, wherein the isopropyl based gel further includes benzyl alcohol, citrate buffer and hydroxyethyl cellulose and has a pH of between 2.5 and 4.0.

10. The method according to claim 1, wherein the ingenol compound is topically applied daily to the seborrheic keratosis lesions for three days.

11. The method according to claim 10, wherein the seborrheic keratosis lesions are cleaned by use of an alcohol swab and air-dried prior to the topical application of the first dose of the ingenol compound.

12. The method according to claim 10, wherein the seborrheic keratosis lesions are cleaned by use of an alcohol swab and air-dried prior to each of the three daily topical applications of the ingenol compound.

13. The method according to claim 10, wherein the seborrheic keratosis lesions treated with the ingenol compound are covered with a dressing after dried following each of the three daily topical applications of the ingenol compound.

14. The method according to claim 10, wherein the seborrheic keratosis lesions are diminished on the length of the longest axis following the topical treatment of the seborrheic keratosis lesions with the ingenol compound.

15. The method according to claim 1, wherein the seborrheic keratosis lesions may be of any size and cover an unlimited skin surface area on the subject.

16. The method according to claim 15, wherein the skin surface area is 500 $mm^2$ or less.

17. The method according to claim 15, wherein the skin surface area is 250 $mm^2$ or less.

18. The method according to claim 15, wherein the skin surface area is 150 $mm^2$ or less.

19. The method according to claim 15, wherein the skin surface area is 100 $mm^2$ or less.

20. The method according to claim 15, wherein the skin surface area is 75 $mm^2$ or less.

21. The method according to claim 15, wherein the skin surface area is 50 $mm^2$ or less.

22. The method according to claim 15, wherein the skin surface area is 25 $mm^2$ or less.

23. The method according to claim 15, wherein the skin surface area is 10 $mm^2$ or less.

24. The method according to claim 2, wherein the ingenol-3-angelate is administered in the form of an isopropyl alcohol based gel.

25. The method according to claim 2, wherein the ingenol-3-angelate is present in a concentration of about 0.05%.

26. The method according to claim 24, wherein the isopropyl based gel further includes benzyl alcohol, a cellulose polymer and a buffer.

27. The method according to claim 24, wherein the cellulose polymer is hydroxyethyl cellulose.

28. The method according to claim 24, wherein the buffer is citrate.

29. The method according to claim 24, wherein the isopropyl based gel has a pH<3.

30. The method according to claim 24, wherein the isopropyl based gel further includes benzyl alcohol, citrate buffer and hydroxyethyl cellulose and has a pH of between 2.5 and 4.0.

31. The method according to claim 2, wherein the ingenol-3-angelate is topically applied daily to the seborrheic keratosis lesions for three days.

32. The method according to claim 31, wherein the method further includes the steps of (a) cleaning the seborrheic keratosis lesions with alcohol prior to the topical application of the first dose of the ingenol-3-angelate, and (b) air-drying drying the cleaned seborrheic keratosis lesions prior to the topical application of the first dose of the ingenol-3-angelate.

33. The method according to claim 31, wherein the method further includes the steps cleaning the seborrheic keratosis lesions with alcohol prior to each of the three daily topical applications of the ingenol-3-angelate, and (b) airdrying drying the cleaned seborrheic keratosis lesions prior to each of the three daily topical applications of the ingenol-3-angelate.

34. The method according to claim 31, wherein the method further includes the steps of (a) drying the treated seborrheic keratosis lesions following each of the three daily topical applications of the ingenol-3-angelate, and (b) covering the dried, treated seborrheic keratosis lesions with a dressing.

35. The method according to claim 22, wherein the seborrheic keratosis lesions are diminished on the length of the longest axis following the topical treatment of the seborrheic keratosis lesions with the ingenol-3-angelate.

36. The method according to claim 2, wherein the seborrheic keratosis lesions may be of any size and cover an unlimited skin surface area on the subject.

37. The method according to claim 36, wherein the skin surface area is 500 mm$^2$ or less.

38. The method according to claim 36, wherein the skin surface area is 250 mm$^2$ or less.

39. The method according to claim 36, wherein the skin surface area is 150 mm$^2$ or less.

40. The method according to claim 36, wherein the skin surface area is 100 mm$^2$ or less.

41. The method according to claim 36, wherein the skin surface area is 75 mm$^2$ or less.

42. The method according to claim 36, wherein the skin surface area is 50 mm$^2$ or less.

43. The method according to claim 36, wherein the skin surface area is 25 mm$^2$ or less.

44. The method according to claim 36, wherein the skin surface area is 10 mm$^2$ or less.

45. A method for the treatment of seborrheic keratosis lesions in a subject,
    the method comprising:
    (a) topically administering a gel to the seborrheic keratosis lesions daily for three consecutive days to treat the seborrheic keratosis lesions;
    (b) swabbing the seborrheic keratosis lesions with alcohol prior to the first topical application of the gel; and
    (c) air-drying the swabbed seborrheic keratosis lesions prior to the first topical application of the gel;
    wherein the seborrheic keratosis lesions are not associated with HPV; and
    wherein the gel includes ingenol-3-angelate in a concentration of about 0.05 and has a pH of between 2.5 and 4.0.

46. The method according to claim 24, wherein the gel further includes benzyl alcohol, isopropyl alcohol, a cellulose polymer and a buffer.

47. A method for the treatment of seborrheic keratosis lesions in a subject,
    the method comprising:
    (a) topically administering a gel to the seborrheic keratosis lesions daily for three consecutive days to treat the seborrheic keratosis lesions;
    (b) swabbing the seborrheic keratosis lesions with alcohol prior to each of the three topical applications of the gel; and
    (c) air-drying the swabbed seborrheic keratosis lesions prior to each of the three topical applications of the gel;
    wherein the seborrheic keratosis lesions are not associated with HPV; and
    wherein the gel includes ingenol-3-angelate in a concentration of about 0.05 and has a pH of between 2.5 and 4.0.

48. The method according to claim 24, wherein the gel further includes benzyl alcohol, isopropyl alcohol, a cellulose polymer and a buffer.

49. A method for the treatment of seborrheic keratosis lesions in a subject, the method comprising:
    (a) topically administering a gel to the seborrheic keratosis lesions daily for three consecutive days to treat the seborrheic keratosis lesions;
    (b) air-drying the treated seborrheic keratosis lesions following each of the three topical administrations of the gel to the seborrheic keratosis lesions; and
    (c) covering the dried seborrheic keratosis lesions with a dressing following each of the three topical applications of the gel;
    wherein the seborrheic keratosis lesions are not associated with HPV; and
    wherein the gel includes ingenol-3-angelate in a concentration of about 0.05 and has a pH of between 2.5 and 4.0.

50. The method according to claim 24, wherein the gel further includes benzyl alcohol, isopropyl alcohol, a cellulose polymer and a buffer.

* * * * *